US007709683B2

(12) United States Patent
Chen et al.

(10) Patent No.: US 7,709,683 B2
(45) Date of Patent: May 4, 2010

(54) SYNTHESIS OF BIS(THIO-HYDRAZIDE AMIDE) SALTS

(75) Inventors: Shoujun Chen, Bedford, MA (US); Zhi-Qiang Xia, Acton, MA (US)

(73) Assignee: Synta Pharmaceuticals Corp., Lexington, MA (US)

( * ) Notice: Subject to any disclaimer, the term of this patent is extended or adjusted under 35 U.S.C. 154(b) by 106 days.

(21) Appl. No.: 11/432,307

(22) Filed: May 11, 2006

(65) Prior Publication Data

US 2006/0270873 A1 Nov. 30, 2006

Related U.S. Application Data

(60) Provisional application No. 60/681,263, filed on May 16, 2005.

(51) Int. Cl.
C07C 241/02 (2006.01)
(52) U.S. Cl. .................. 564/148; 564/149; 564/151; 564/74
(58) Field of Classification Search .............. 564/148, 564/149, 151, 74
See application file for complete search history.

(56) References Cited

U.S. PATENT DOCUMENTS

| 4,012,360 | A | 3/1977 | Schwarzenbach et al. |
| 6,013,836 | A | 1/2000 | Hsu et al. |
| 6,172,108 | B1 | 1/2001 | Vega et al. |
| 6,172,188 | B1 | 1/2001 | Thastrup et al. |
| 6,235,787 | B1 | 5/2001 | Broadhurst et al. |
| 6,365,745 | B1 | 4/2002 | Matsui et al. |
| 6,399,659 | B2 | 6/2002 | Usui et al. |
| 6,435,787 | B1 | 8/2002 | John |
| 6,455,515 | B2 | 9/2002 | Gypser et al. |
| 6,656,971 | B2 | 12/2003 | Wu et al. |
| 6,703,426 | B1 | 3/2004 | Miles et al. |
| 6,762,204 | B2 * | 7/2004 | Koya et al. ............ 514/599 |
| 6,800,660 | B2 | 10/2004 | Koya et al. |
| 6,825,235 | B2 | 11/2004 | Chen et al. |
| 6,924,312 | B2 | 8/2005 | Koya et al. |
| 7,001,923 | B2 | 2/2006 | Koya et al. |
| 7,037,940 | B2 | 5/2006 | Koya et al. |
| 7,074,952 | B2 | 7/2006 | Chen et al. |
| 2003/0045518 | A1 | 3/2003 | Koya et al. |
| 2003/0119914 | A1 | 6/2003 | Koya et al. |
| 2004/0022869 | A1 | 2/2004 | Chen et al. |
| 2004/0225016 | A1 | 11/2004 | Koya et al. |
| 2006/0116374 | A1 | 6/2006 | Koya et al. |
| 2006/0122183 | A1 | 6/2006 | Koya et al. |
| 2006/0135595 | A1 | 6/2006 | Koya et al. |
| 2006/0142386 | A1 | 6/2006 | Barsoum |
| 2006/0142393 | A1 | 6/2006 | Sherman et al. |
| 2006/0281811 | A1 | 12/2006 | Chen et al. |
| 2007/0088057 | A1 | 4/2007 | Lunsmann et al. |

FOREIGN PATENT DOCUMENTS

| DE | 2037257 | 2/1972 |
| FR | 2097737 | 4/1972 |
| JP | 50-91056 | 7/1975 |
| WO | WO 94/10995 A1 | 5/1994 |
| WO | WO 99/34796 A1 | 7/1999 |
| WO | WO 03/006428 A1 | 1/2003 |
| WO | WO 03/006430 A1 | 1/2003 |
| WO | WO 2004/064826 A1 | 8/2004 |
| WO | WO 2006/009940 A1 | 1/2006 |
| WO | WO 2006/033913 A2 | 3/2006 |
| WO | WO 2006/113493 A2 | 10/2006 |
| WO | WO 2006/113572 A1 | 10/2006 |
| WO | WO 2006/113695 A1 | 10/2006 |

OTHER PUBLICATIONS

"Remarks" paper as submitted by applicant's attorney.
Al-Talib, M. et al., "Diacyl Acid Dihydrazides," Magnetic Resonance in Chemistry 28:1072-1078 (1990).
Asahi Chemical Ind. KK. Abstract of Japanese Patent No. 50-91056, Accession No. 47521Y/27 (1975).
Barrett, William G. and McKay, Donald, "Decomposition and Cycloaddition Reactions of Some Bis(azodicarbonyl) Compounds," Journal of Chem. Soc. (4):1046-1052 (1975).
Barry, V. C., et al., "Anticancer Agents—III. Synthesis and Anticancer Activity of Some Bis-Thiosemicarbazones and Thoiosemicarbazides," Proc. R.I.A. Sect. B(65):309-324 (1967).
Chuiguk, V.A., and Nemazanyi, A.G., "Mesoionic Methine Dyes Of Biquaternary Salts Of Diheteroaryl Methanes—Derivatives Of 1, 3, 4—oxa (thia) Diazoles and 1, 2, 4—Triazoles," Kiev. Gos. Univ., Kiev, USSR, Ukrainskii Khimicheskii Zhurnal, Russian Edition, 50(5):519-524 (1984). Abstract, Accession No. 1984:630420, HCAPLUS Database.

(Continued)

*Primary Examiner*—Peter G O'Sullivan
*Assistant Examiner*—Sudhakar Katakam
(74) *Attorney, Agent, or Firm*—Foley & Lardner LLP; Steven G. Davis

(57) ABSTRACT

A method of preparing a bis(thio-hydrazide amide) disalt includes the steps of combining a neutral bis(thio-hydrazide amide), an organic solvent and a base to form a bis(thio-hydrazide amide) solution; and combining the solution and methyl tert-butyl ether, thereby precipitating a disalt of the bis(thio-hydrazide amide).

In some embodiments, a method of preparing a bis(thio-hydrazide amide) disalt includes the steps of combining a neutral bis(thio-hydrazide amide) and an organic solvent selected from methanol, ethanol, acetone, and methyl ethyl ketone to make a mixture; adding at least two equivalents of a base selected from sodium hydroxide, potassium hydroxide, sodium methoxide, potassium methoxide, sodium ethoxide and potassium ethoxide to the mixture, thereby forming a solution; and combining the solution and methyl tert-butyl ether to precipitate the disalt of the bis(thio-hydrazide amide).

The disclosed methods do not require lyophilization and the solvents used in the process can be more readily removed to low levels consistent with pharmaceutically acceptable preparation.

25 Claims, No Drawings

OTHER PUBLICATIONS

Chuyguk, V. A. and Nemazanyj A.G., "Mesoionic Methine Dyes from Biquaternary Salts of Dihetarylmethanes—1,3,4-Oxa(thia)diazoles and 1,2,4-Triazoles Derivatives," *Ukr. Khim. Zhurn.* 48:520 (1984).

H. Bräuniger, "Hydrazide und Hydrazidderivate von Dicarbonsäuren," Pharmaceutical-Chemical Institute of University of Rostock, Supplied by the "British Library" 25(5-6) 279-283 (1970).

Honshu Paper Mfg. Co. Ltd, Abstract of Japanese Patent No. 182050, published Feb. 13, 1996.

Merlin, J.L., et al., In Vitro Comparative Evaluation of Trastuzumab (Herceptin®) Combined with Paclitaxel (Taxol®) or Docetaxel (Taxotere®) in HER2-Expressing Human Breast Cancer Cell Lines, *Annals of Oncology 13*: 1743-1748 (2002).

Mitsui Toatsu Chem. Inc., Abstract of Japanese Patent No. 308024, published Dec. 25, 1986. from Derwent Publications Ltd.

Molina, P., et al., XP-001118802 "Preparation of a Novel Type of Ligands Incorporating Two or Three 1,3,4-Thiadiazole Units," *Heterocycles 36*(6):1263-1278 (1993).

Molina, P., et al., XP-01118868 "Methyl 2-Methyldithiocarbazate in Heterocyclic Synthesis: Preparation of 2,5-Disubstituted 1,3,4-Thiadiazoles, Bis(1,3,4-Thiadiazolium) Salts and Macrocycles containing 1,3,4-Thiadiazole Subunits, X-Ray Crystal Structure of 2,2'-Bis[4,5-dihydro-5-(2-hydroxyethylimino)-4-methyl-1,3,4-thiadiazole]," *J. Chem. Soc. Perkin Trans. 1 s* 5:1159-1166 (1991).

O'Callaghan, C. N., "Anticancer Agents—X. Cyclisation of 1-Acyl-4-Alkylthiosemicarbazide Derivatives to 1,2,4-Triazoline-3-Thiones in the Presence of Hydrazine," *Proc. R.I.A.*, Sect. B(74):455-461 (1974).

Rupp, Walter, CA76:126992, 1972.

Schwarz et al., CA77:48081, 1972.

Stalteri, M.A., et al., "Site-specific conjugation and labelling of prostate antibody 7E11C5.3 (CYT-351) with technetium-99m," *European Journal of Nuclear Medicine* 24(6):651-654, (1997).

Twomey, D., "Anticancer Agents-IX. Derivatives of Pyridine, Pyridazine and Phthalazine," *Proceedings of the Royal Irish Academy*, vol. 74, Sect. B:37-52,(1974).

* cited by examiner

SYNTHESIS OF BIS(THIO-HYDRAZIDE AMIDE) SALTS

RELATED APPLICATION

This application claims the benefit of U.S. Provisional Application No. 60/681,263, filed on May 16, 2005. The entire teachings of the above application are incorporated herein by reference.

BACKGROUND OF THE INVENTION

Certain bis(thio-hydrazide amide) compounds are useful as pharmaceuticals, in particular, as anticancer agents. See, for example Chen, et al., U.S. Pat. No. 6,825,235, U.S. Published Patent Application No. 20040229952; U.S. Pat. Nos. 6,762,204 and 6,800,660 to Koya, et al., and U.S. Published Patent Application Nos. 20050009920, 20040235909, 20040225016, and 20030195258. The entire teachings of these documents are incorporated by reference.

Salts of these bis(thio-hydrazide amide) compounds are believed to be particularly useful at least in part for reasons of solubility. See, for example Koya, et al., U.S. Provisional Patent Application Ser. No. 60/582,596, filed Jun. 23, 2004, and U.S. Provisional Patent Application Ser. No. 60/681,368, filed concurrently herewith. The entire teachings of these applications are incorporated by reference. However, the existing process includes a lyophilization step, which can be energy intensive and poorly suited to scale up to production runs.

Therefore, there is a need for an improved process for preparing salts of bis(thio-hydrazide amide) compounds.

SUMMARY OF THE INVENTION

It has now been found that bis(thio-hydrazide amide) disalts can be prepared in a process suitable for scale-up to pharmaceutical production runs.

A method of preparing a bis(thio-hydrazide amide) disalt includes the steps of combining a neutral bis(thio-hydrazide amide), an organic solvent and a base to form a bis(thio-hydrazide amide) solution; and combining the solution and methyl tert-butyl ether, thereby precipitating a disalt of the bis(thio-hydrazide amide).

In some embodiments, a method of preparing a bis(thio-hydrazide amide) disalt includes the steps of combining a neutral bis(thio-hydrazide amide) and an organic solvent selected from methanol, ethanol, acetone, and methyl ethyl ketone to make a mixture; adding at least two equivalents of a base selected from sodium hydroxide, potassium hydroxide, sodium methoxide, potassium methoxide, sodium ethoxide and potassium ethoxide to the mixture, thereby forming a solution; and combining the solution and methyl tert-butyl ether to precipitate the disalt of the bis(thio-hydrazide amide).

The disclosed methods do not require lyophilization and the solvents used in the process can be more readily removed to low levels consistent with pharmaceutically acceptable preparation.

DETAILED DESCRIPTION OF THE INVENTION

A description of preferred embodiments of the invention follows. The invention is a method of preparing a bis(thio-hydrazide amide) disalt, which includes the steps of combining a neutral bis(thio-hydrazide amide), an organic solvent and a base to form a bis(thio-hydrazide amide) solution; and combining the solution and methyl tert-butyl ether, thereby precipitating a disalt of the bis(thio-hydrazide amide). Thus, as used herein, a neutral bis(thio-hydrazide amide) has at least two hydrogens which can react with the bases described herein to form a disalt.

Typically, at least about two molar equivalents of the base are employed for each molar equivalent of neutral bis(thio-hydrazide amide); more typically, from about 2 to about 5 equivalents, or preferably from about 2.0 to about 2.5 equivalents.

Suitable bases can be strong enough to react with a bis(thio-hydrazide amide) to produced a disalt. In various embodiments, the base can be an amine (e.g., triethylamine, diphenylamine, butylamine, or the like); an ammonium hydroxide (e.g., tetramethylammonium hydroxide, tetrabutylammonium hydroxide, or the like); an alkali metal hydroxide (lithium hydroxide, sodium hydroxide, potassium hydroxide, or the like) an alkali metal C1-C6 alkoxide, or an alkali metal amide (e.g., sodium amide, lithium diisopropyl amide, or the like). In some embodiments, the base is sodium hydroxide, potassium hydroxide, sodium C1-C6 alkoxide, potassium C1-C6 alkoxide, sodium amide, or potassium amide, or preferably, sodium hydroxide, sodium methoxide, or sodium ethoxide.

In various embodiments, the base can be an alkali metal hydride (e.g., sodium hydride, potassium hydride, or the like), a divalent metal base (e.g., magnesium oxide) a C1-C6 alkyl alkali metal (e.g., butyllithium), or an aryl alkali metal (e.g., phenyllithium). More typically, the base is lithium hydride, sodium hydride, potassium hydride, butyllithium, butylsodium, butylpotassium, phenyllithium, phenylsodium, or phenylpotassium.

As used herein, an alkali metal includes lithium, sodium, potassium, cesium and rubidium.

The organic solvent can be any organic solvent which is stable when the base is added to a mixture of the bis(thio-hydrazide amide) and the organic solvent. Typically, the organic solvent is polar enough to dissolve the bis(thio-hydrazide amide) salt formed by the method to form a solution. In various embodiments, the organic solvent is water-miscible. The organic solvent can generally be selected from a C1-C4 aliphatic alcohol (e.g., methanol, ethanol, 1-propanol, 2-propanol, or the like), a C1-C4 aliphatic ketone (e.g., acetone, methyl ethyl ketone, 2-butanone, or the like), a C2-C4 aliphatic ether (e.g., diethyl ether, dipropyl ether, diisopropyl ether, or the like), a C2-C4 cycloaliphatic ether (e.g., tetrahydrofuran, dioxane), dimethyl formamide, dimethyl sulfoxide, N-methylpyrrolidone, a glycol (e.g., ethylene glycol, propylene glycol, tetramethylene glycol, or the like), an alkyl glycol ether (e.g., ethylene glycol dimethyl ether, or the like), and acetonitrile. More typically, the organic solvent can be selected from methanol, ethanol, propanol (e.g., 1-propanol, 2-propanol), butanol (e.g., 1-butanol, tert-butyl alcohol, or the like), acetone, tetrahydrofuran, and methyl ethyl ketone. Preferably, the organic solvent can be selected from methanol, ethanol, acetone, and methyl ethyl ketone.

In various embodiments, the neutral bis(thio-hydrazide amide) can be substantially insoluble in the organic solvent, thereby forming a mixture, whereby combining the base with the mixture forms a bis(thio-hydrazide amide) solution. Typically, the bis(thio-hydrazide amide) solution can be clear. Generally, between about 0.25 and about 2.5 moles of the neutral bis(thio-hydrazide amide) are combined per each liter of organic solvent, or typically between about 0.75 and about 1.5 moles of the neutral bis(thio-hydrazide amide) are combined per each liter of organic solvent. Preferably, about 1 mole of the neutral bis(thio-hydrazide amide) are combined per each liter of organic solvent.

As used herein, a "bis(thio-hydrazide amide) solution," when formed from the organic solvent, the neutral bis(thio-hydrazide amide), and the base, can include one or more species such as the neutral bis(thio-hydrazide amide), the bis(thio-hydrazide amide) monosalt, the bis(thio-hydrazide amide) disalt, or the like.

In preferred embodiments, the organic solvent is ethanol. Preferably, the base is about 2 molar to about 5 molar aqueous sodium hydroxide, or more preferably from about 2 to about 2.5 molar.

In preferred embodiments, the organic solvent is acetone. Preferably, the base is about 2 molar to about 5 molar ethanolic sodium ethoxide, or more preferably from about 2 to about 2.5 molar.

The neutral bis(thio-hydrazide amides) employed in the disclosed method can be represented by Structural Formula I:

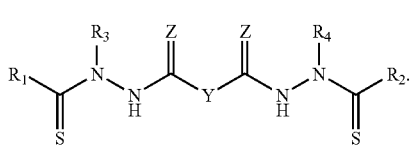

(I)

Y is a covalent bond or an optionally substituted straight chained hydrocarbyl group.

$R_1$-$R_4$ are independently —H, an optionally substituted aliphatic group, an optionally substituted aryl group, or $R_1$ and $R_3$ taken together with the carbon and nitrogen atoms to which they are bonded, and/or $R_2$ and $R_4$ taken together with the carbon and nitrogen atoms to which they are bonded, form a non-aromatic heterocyclic ring optionally fused to an aromatic ring.

Z is O or S.

The neutral bis(thiohydrazide) amides can be prepared according to methods described in U.S. Pat. No. 6,825,235 to Chen, et al., and U.S. Pat. Nos. 6,762,204 and 6,800,660 to Koya, et al., and also according to methods described in the co-pending and co-owned U.S. Published Patent Application No. US20030195258, Published: Oct. 16, 2003 and U.S. patent application Ser. No. 10/758,589, Jan. 15, 2004. The entire teachings of each document referred to in this application is expressly incorporated herein by reference. Examples of Structural Formulas representing the salts and tautomers thereof produced by the disclosed method are given in Koya, et al., U.S. Provisional Patent Application Ser. No. 60/582, 596, filed Jun. 23, 2004, the entire teachings of which are incorporated herein by reference.

In one embodiment, Y in Structural Formula I is a covalent bond, —C($R_5R_6$)—, —(CH$_2$CH$_2$)—, trans-(CH=CH)—, cis-(CH=CH)— or —(C≡C)— group, preferably —C($R_5R_6$)—. $R_1$-$R_4$ are as described above for Structural Formula I. $R_5$ and $R_6$ are each independently —H, an aliphatic or substituted aliphatic group, or $R_5$ is —H and $R_6$ is an optionally substituted aryl group, or, $R_5$ and $R_6$, taken together, are an optionally substituted C2-C6 alkylene group. The pharmaceutically acceptable cation is as described in detail below.

In particular embodiments, the bis(thio-hydrazide amides) are represented by Structural Formula II:

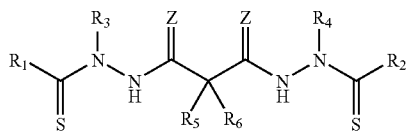

II $R_1$-$R_6$ and the pharmaceutically acceptable cation are as described above for Structural Formula I.

In Structural Formulas I-II, $R_1$ and $R_2$ are the same or different and/or $R_3$ and $R_4$ are the same or different; preferably, $R_1$ and $R_2$ are the same and $R_3$ and $R_4$ are the same. In Structural Formulas I and II, Z is preferably O. Typically in Structural Formulas I and II, Z is O; $R_1$ and $R_2$ are the same; and $R_3$ and $R_4$ are the same. More preferably, Z is O; $R_1$ and $R_2$ are the same; $R_3$ and $R_4$ are the same.

In other embodiments, the bis(thio-hydrazide amides) are represented by Structural Formula II: $R_1$ and $R_2$ are each an optionally substituted aryl group, preferably an optionally substituted phenyl group; $R_3$ and $R_4$ are each an optionally substituted aliphatic group, preferably an alkyl group, more preferably, methyl or ethyl; and $R_5$ and $R_6$ are as described above, but $R_5$ is preferably —H and $R_6$ is preferably —H, an aliphatic or substituted aliphatic group.

Alternatively, $R_1$ and $R_2$ are each an optionally substituted aryl group; $R_3$ and $R_4$ are each an optionally substituted aliphatic group; $R_5$ is —H; and $R_6$ is —H, an aliphatic or substituted aliphatic group. Preferably, $R_1$ and $R_2$ are each an optionally substituted aryl group; $R_3$ and $R_4$ are each an alkyl group; and $R_5$ is —H and $R_6$ is —H or methyl. Even more preferably, $R_1$ and $R_2$ are each an optionally substituted phenyl group; $R_3$ and $R_4$ are each methyl or ethyl; and $R_5$ is —H and $R_6$ is —H or methyl. Suitable substituents for an aryl group represented by $R_1$ and $R_2$ and an aliphatic group represented by $R_3$, $R_4$ and $R_6$ are as described below for aryl and aliphatic groups.

In another embodiment, the bis(thio-hydrazide amides) are represented by Structural Formula II: $R_1$ and $R_2$ are each an optionally substituted aliphatic group, preferably a C3-C8 cycloalkyl group optionally substituted with at least one alkyl group, more preferably cyclopropyl or 1-methylcyclopropyl; $R_3$ and $R_4$ are as described above for Structural Formula I, preferably both an optionally substituted alkyl group; $R_5$ and $R_6$ are as described above, but $R_5$ is preferably —H and $R_6$ is preferably —H, an aliphatic or substituted aliphatic group, more preferably —H or methyl.

Alternatively, the bis(thio-hydrazide amides) are represented by Structural Formula II: $R_1$ and $R_2$ are each an optionally substituted aliphatic group; $R_3$ and $R_4$ are as described above for Structural Formula I, preferably both an optionally substituted alkyl group; and $R_5$ is —H and $R_6$ is —H or an optionally substituted aliphatic group. Preferably, $R_1$ and $R_2$ are both a C3-C8 cycloalkyl group optionally substituted with at least one alkyl group; $R_3$ and $R_4$ are both as described above for Structural Formula I, preferably an alkyl group; and $R_5$ is —H and $R_6$ is —H or an aliphatic or substituted aliphatic group. More preferably, $R_1$ and $R_2$ are both a C3-C8 cycloalkyl group optionally substituted with at least one alkyl group; $R_3$ and $R_4$ are both an alkyl group; and $R_5$ is —H and $R_6$ is —H or methyl. Even more preferably, $R_1$ and $R_2$ are both cyclopropyl or 1-methylcyclopropyl; $R_3$ and $R_4$ are both an alkyl group, preferably methyl or ethyl; and $R_5$ is —H and $R_6$ is —H or methyl.

In specific embodiments, the bis(thio-hydrazide amides) are represented by Structural Formula III:

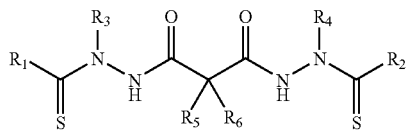

III wherein: $R_1$ and $R_2$ are both phenyl, $R_3$ and $R_4$ are both methyl, and $R_5$ and $R_6$ are both —H; $R_1$ and $R_2$ are both phenyl, $R_3$ and $R_4$ are both ethyl, and $R_5$ and $R_6$ are both —H; $R_1$ and $R_2$ are both 4-cyanophenyl, $R_3$ and $R_4$ are both methyl, $R_5$ is methyl, and $R_6$ is —H; $R_1$ and $R_2$ are both 4-methoxyphenyl, $R_3$ and $R_4$ are both methyl, and $R_5$ and $R_6$ are both —H; $R_1$ and $R_2$ are both phenyl, $R_3$ and $R_4$ are both methyl, $R_5$ is methyl, and $R_6$ is —H; $R_1$ and $R_2$ are both phenyl, $R_3$ and $R_4$ are both ethyl, $R_5$ is methyl, and $R_6$ is —H; $R_1$ and $R_2$ are both 4-cyanophenyl, $R_3$ and $R_4$ are both methyl, and $R_5$ and $R_6$ are both —H; $R_1$ and $R_2$ are both 2,5-dimethoxyphenyl, $R_3$ and $R_4$ are both methyl, and $R_5$ and $R_6$ are both —H; $R_1$ and $R_2$ are both 2,5-dimethoxyphenyl, $R_3$ and $R_4$ are both methyl, $R_5$ is methyl, and $R_6$ is —H; $R_1$ and $R_2$ are both 3-cyanophenyl, $R_3$ and $R_4$ are both methyl, and $R_5$ and $R_6$ are both —H; $R_1$ and $R_2$ are both 3-fluorophenyl, $R_3$ and $R_4$ are both methyl, and $R_5$ and $R_6$ are both —H; $R_1$ and $R_2$ are both 4-chlorophenyl, $R_3$ and $R_4$ are both methyl, $R_5$ is methyl, and $R_6$ is —H; $R_1$ and $R_2$ are both 2-dimethoxyphenyl, $R_3$ and $R_4$ are both methyl, and $R_5$ and $R_6$ are both —H; $R_1$ and $R_2$ are both 3-methoxyphenyl, $R_3$ and $R_4$ are both methyl, and $R_5$ and $R_6$ are both —H; $R_1$ and $R_2$ are both 2,3-dimethoxyphenyl, $R_3$ and $R_4$ are both methyl, and $R_5$ and $R_6$ are both —H; $R_1$ and $R_2$ are both 2,3-dimethoxyphenyl, $R_3$ and $R_4$ are both methyl, $R_5$ is methyl, and $R_6$ is —H; $R_1$ and $R_2$ are both 2,5-difluorophenyl, $R_3$ and $R_4$ are both methyl, and $R_5$ and $R_6$ are both —H; $R_1$ and $R_2$ are both 2,5-difluorophenyl, $R_3$ and $R_4$ are both methyl, $R_5$ is methyl, and $R_6$ is —H; $R_1$ and $R_2$ are both 2,5-dichlorophenyl, $R_3$ and $R_4$ are both methyl, and $R_5$ and $R_6$ are both —H; $R_1$ and $R_2$ are both 2,5-dimethylphenyl, $R_3$ and $R_4$ are both methyl, and $R_5$ and $R_6$ are both —H; $R_1$ and $R_2$ are both 2,5-dimethoxyphenyl, $R_3$ and $R_4$ are both methyl, and $R_5$ and $R_6$ are both —H; $R_1$ and $R_2$ are both phenyl, $R_3$ and $R_4$ are both methyl, and $R_5$ and $R_6$ are both —H; $R_1$ and $R_2$ are both 2,5-dimethoxyphenyl, $R_3$ and $R_4$ are both methyl, $R_5$ is methyl, and $R_6$ is —H; $R_1$ and $R_2$ are both cyclopropyl, $R_3$ and $R_4$ are both methyl, and $R_5$ and $R_6$ are both —H; $R_1$ and $R_2$ are both cyclopropyl, $R_3$ and $R_4$ are both ethyl, and $R_5$ and $R_6$ are both —H; $R_1$ and $R_2$ are both cyclopropyl, $R_3$ and $R_4$ are both methyl, $R_5$ is methyl, and $R_6$ is —H; $R_1$ and $R_2$ are both 1-methylcyclopropyl, $R_3$ and $R_4$ are both methyl, and $R_5$ and $R_6$ are both —H; $R_1$ and $R_2$ are both 1-methylcyclopropyl, $R_3$ and $R_4$ are both methyl, $R_5$ is methyl and $R_6$ is —H; $R_1$ and $R_2$ are both 1-methylcyclopropyl, $R_3$ and $R_4$ are both methyl, $R_5$ is ethyl, and $R_6$ is —H; $R_1$ and $R_2$ are both 1-methylcyclopropyl, $R_3$ and $R_4$ are both methyl, $R_5$ is n-propyl, and $R_6$ is —H; $R_1$ and $R_2$ are both 1-methylcyclopropyl, $R_3$ and $R_4$ are both methyl, and $R_5$ and $R_6$ are both methyl; $R_1$ and $R_2$ are both 1-methylcyclopropyl, $R_3$ and $R_4$ are both ethyl, and $R_5$ and $R_6$ are both —H; $R_1$ and $R_2$ are both 1-methylcyclopropyl, $R_3$ is methyl, $R_4$ is ethyl, and $R_5$ and $R_6$ are both —H; $R_1$ and $R_2$ are both 2-methylcyclopropyl, $R_3$ and $R_4$ are both methyl, and $R_5$ and $R_6$ are both —H; $R_1$ and $R_2$ are both 2-phenylcyclopropyl, $R_3$ and $R_4$ are both methyl, and $R_5$ and $R_6$ are both —H; $R_1$ and $R_2$ are both 1-phenylcyclopropyl, $R_3$ and $R_4$ are both methyl, and $R_5$ and $R_6$ are both —H; $R_1$ and $R_2$ are both cyclobutyl, $R_3$ and $R_4$ are both methyl, and $R_5$ and $R_6$ are both —H; $R_1$ and $R_2$ are both cyclopentyl, $R_3$ and $R_4$ are both methyl, and $R_5$ and $R_6$ are both —H; $R_1$ and $R_2$ are both cyclohexyl, $R_3$ and $R_4$ are both methyl, and $R_5$ and $R_6$ are both —H; $R_1$ and $R_2$ are both cyclohexyl, $R_3$ and $R_4$ are both phenyl, and $R_5$ and $R_6$ are both —H; $R_1$ and $R_2$ are both methyl, $R_3$ and $R_4$ are both methyl, and $R_5$ and $R_6$ are both —H; $R_1$ and $R_2$ are both methyl, $R_3$ and $R_4$ are both t-butyl, and $R_5$ and $R_6$ are both —H; $R_1$ and $R_2$ are both phenyl, and $R_5$ and $R_6$ are both —H; $R_1$ and $R_2$ are both t-butyl, $R_3$ and $R_4$ are both methyl, and $R_5$ and $R_6$ are both —H; $R_1$ and $R_2$ are ethyl, $R_3$ and $R_4$ are both methyl, and $R_5$ and $R_6$ are both —H; or $R_1$ and $R_2$ are both n-propyl, $R_3$ and $R_4$ are both methyl, and $R_5$ and $R_6$ are both —H.

In specific embodiments, the bis(thio-hydrazide amides) are represented by Structural Formula IV:

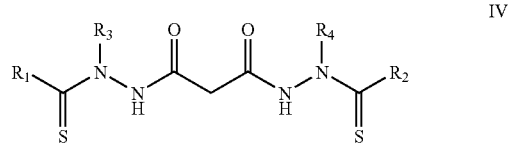

IV wherein: $R_1$ and $R_2$ are both phenyl, and $R_3$ and $R_4$ are both o-CH$_3$-phenyl; $R_1$ and $R_2$ are both o-CH$_3$C(O)O-phenyl, and $R_3$ and $R_4$ are phenyl; $R_1$ and $R_2$ are both phenyl, and $R_3$ and $R_4$ are both methyl; $R_1$ and $R_2$ are both phenyl, and $R_3$ and $R_4$ are both ethyl; $R_1$ and $R_2$ are both phenyl, and $R_3$ and $R_4$ are both n-propyl; $R_1$ and $R_2$ are both p-cyanophenyl, and $R_3$ and $R_4$ are both methyl; $R_1$ and $R_2$ are both p-nitro phenyl, and $R_3$ and $R_4$ are both methyl; $R_1$ and $R_2$ are both 2,5-dimethoxyphenyl, and $R_3$ and $R_4$ are both methyl; $R_1$ and $R_2$ are both phenyl, and $R_3$ and $R_4$ are both n-butyl; $R_1$ and $R_2$ are both p-chlorophenyl, and $R_3$ and $R_4$ are both methyl; $R_1$ and $R_2$ are both 3-nitrophenyl, and $R_3$ and $R_4$ are both methyl; $R_1$ and $R_2$ are both 3-cyanophenyl, and $R_3$ and $R_4$ are both methyl; $R_1$ and $R_2$ are both 3-fluorophenyl, and $R_3$ and $R_4$ are both methyl; $R_1$ and $R_2$ are both 2-furanyl, and $R_3$ and $R_4$ are both phenyl; $R_1$ and $R_2$ are both 2-methoxyphenyl, and $R_3$ and $R_4$ are both methyl; $R_1$ and $R_2$ are both 3-methoxyphenyl, and $R_3$ and $R_4$ are both methyl; $R_1$ and $R_2$ are both 2,3-dimethoxyphenyl, and $R_3$ and $R_4$ are both methyl; $R_1$ and $R_2$ are both 2-methoxy-5-chlorophenyl, and $R_3$ and $R_4$ are both ethyl; $R_1$ and $R_2$ are both 2,5-difluorophenyl, and $R_3$ and $R_4$ are both methyl; $R_1$ and $R_2$ are both 2,5-dichlorophenyl, and $R_3$ and $R_4$ are both methyl; $R_1$ and $R_2$ are both 2,5-dimethylphenyl, and $R_3$ and $R_4$ are both methyl; $R_1$ and $R_2$ are both 2-methoxy-5-chlorophenyl, and $R_3$ and $R_4$ are both methyl; $R_1$ and $R_2$ are both 3,6-dimethoxyphenyl, and $R_3$ and $R_4$ are both methyl; $R_1$ and $R_2$ are both phenyl, and $R_3$ and $R_4$ are both 2-ethylphenyl; $R_1$ and $R_2$ are both 2-methyl-5-pyridyl, and $R_3$ and $R_4$ are both methyl; or $R_1$ is phenyl; $R_2$ is 2,5-dimethoxyphenyl, and $R_3$ and $R_4$ are both methyl; $R_1$ and $R_2$ are both methyl, and $R_3$ and $R_4$ are both p-CF$_3$-phenyl; $R_1$ and $R_2$ are both methyl, and $R_3$ and $R_4$ are both o-CH$_3$-phenyl; $R_1$ and $R_2$ are both —(CH$_2$)$_3$COOH; and $R_3$ and $R_4$ are both phenyl; $R_1$ and $R_2$ are both represented by the following structural formula:

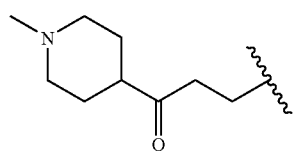

and $R_3$ and $R_4$ are both phenyl; $R_1$ and $R_2$ are both n-butyl, and $R_3$ and $R_4$ are both phenyl; $R_1$ and $R_2$ are both n-pentyl, $R_3$ and $R_4$ are both phenyl; $R_1$ and $R_2$ are both methyl, and $R_3$ and $R_4$ are both 2-pyridyl; $R_1$ and $R_2$ are both cyclohexyl, and $R_3$ and $R_4$ are both phenyl; $R_1$ and $R_2$ are both methyl, and $R_3$ and $R_4$ are both 2-ethylphenyl; $R_1$ and $R_2$ are both methyl, and $R_3$ and $R_4$ are both 2,6-dichlorophenyl; $R_1$-$R_4$ are all methyl; $R_1$ and $R_2$ are both methyl, and $R_3$ and $R_4$ are both t-butyl; $R_1$ and $R_2$ are both ethyl, and $R_3$ and $R_4$ are both methyl; $R_1$ and $R_2$ are both t-butyl, and $R_3$ and $R_4$ are both methyl; $R_1$ and $R_2$ are both cyclopropyl, and $R_3$ and $R_4$ are both methyl; $R_1$ and $R_2$ are both cyclopropyl, and $R_3$ and $R_4$ are both ethyl; $R_1$ and $R_2$ are both 1-methylcyclopropyl, and $R_3$ and $R_4$ are both methyl; $R_1$ and $R_2$ are both 2-methylcyclopropyl, and $R_3$ and $R_4$ are both methyl; $R_1$ and $R_2$ are both 1-phenylcyclopropyl, and $R_3$ and $R_4$ are both methyl; $R_1$ and $R_2$ are both 2-phenylcyclopropyl, and $R_3$ and $R_4$ are both methyl; $R_1$ and $R_2$ are both cyclobutyl, and $R_3$ and $R_4$ are both methyl; $R_1$ and $R_2$ are both cyclopentyl, and $R_3$ and $R_4$ are both methyl; $R_1$ is cyclopropyl, $R_2$ is phenyl, and $R_3$ and $R_4$ are both methyl.

Preferred examples of bis(thio-hydrazide amides) include Compounds (1)-(18) and pharmaceutically acceptable salts and solvates thereof:

Compound (1)
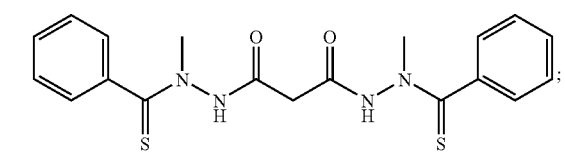

Compound (2)
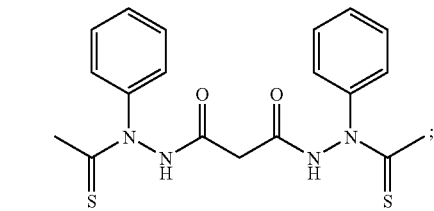

Compound (3)
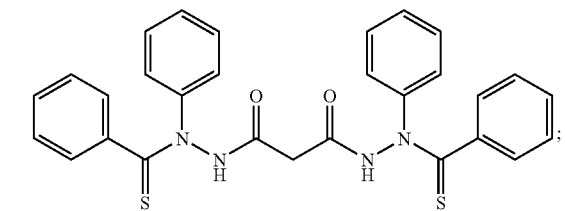

Compound (4)
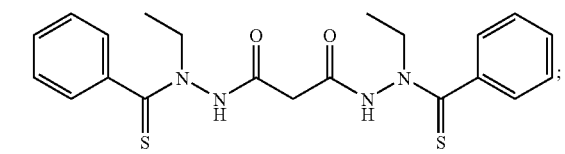

Compound (5)
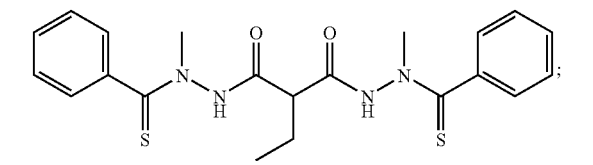

Compound (6)
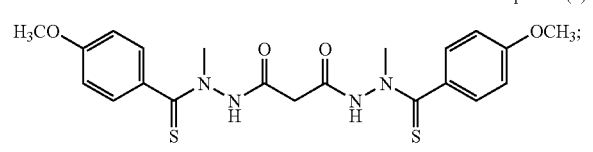

-continued

Compound (7)
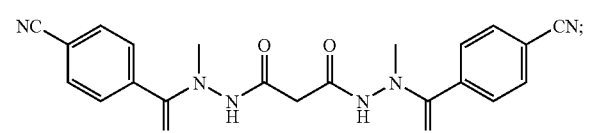

Compound (8)
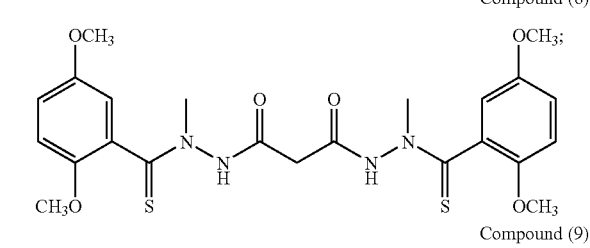

Compound (9)
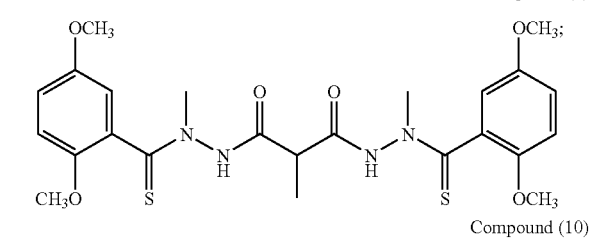

Compound (10)
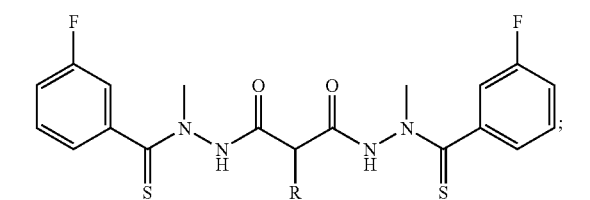

Compound (11)
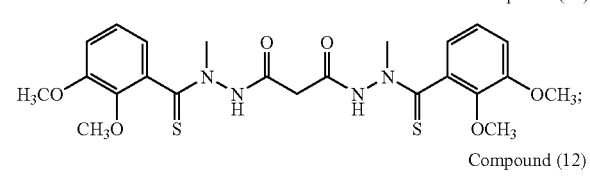

Compound (12)
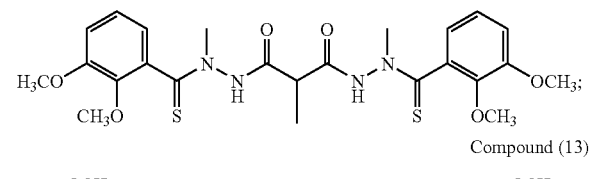

Compound (13)
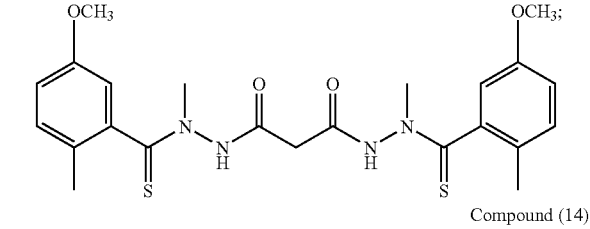

Compound (14)
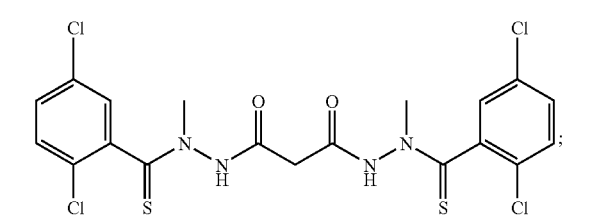

-continued

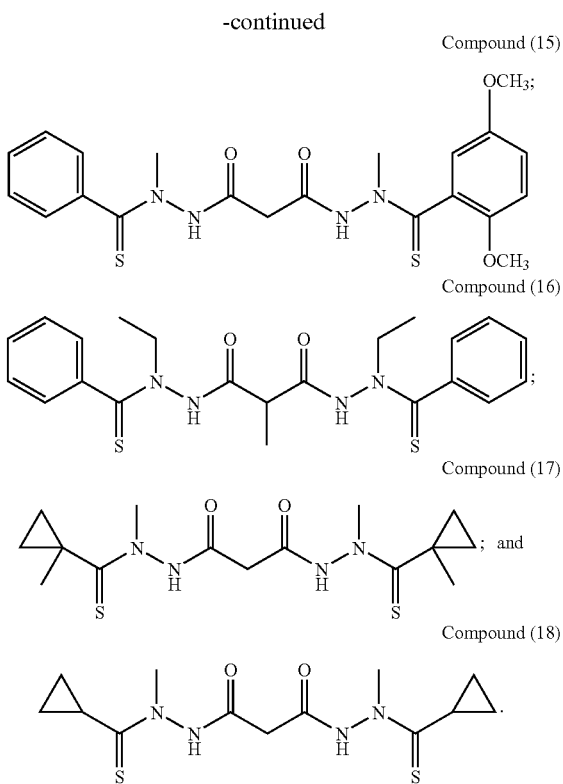

Compound (15)

Compound (16)

Compound (17)

Compound (18)

Particular examples of bis(thio-hydrazide amides) include Compounds (1), (17), and (18).

In some embodiments, a method of preparing a bis(thio-hydrazide amide) disalt includes the steps of combining a neutral bis(thio-hydrazide amide) and an organic solvent selected from methanol, ethanol, acetone, and methyl ethyl ketone to make a mixture; adding at least two equivalents of a base selected from sodium hydroxide, potassium hydroxide, sodium methoxide, potassium methoxide, sodium ethoxide and potassium ethoxide to the mixture, thereby forming a solution; and combining the solution and methyl tert-butyl ether to precipitate the disalt of the bis(thio-hydrazide amide). In preferred embodiments: the organic solvent is acetone; the base is ethanolic sodium ethoxide; the organic solvent is ethanol; the base is aqueous sodium hydroxide; the neutral bis(thio-hydrazide amide) is:

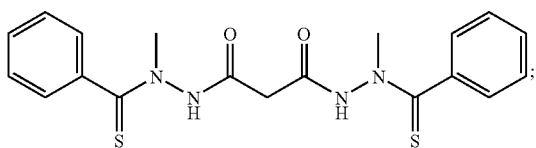

and/or the neutral bis(thio-hydrazide amide) is:

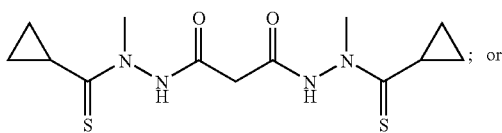

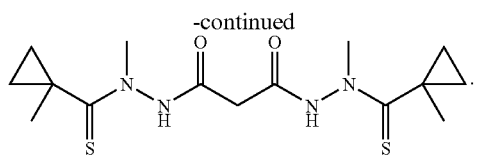

A "straight chained hydrocarbyl group" is an alkylene group, i.e., $-(CH_2)_y-$, with one, or more (preferably one) internal methylene groups optionally replaced with a linkage group. y is a positive integer (e.g., between 1 and 10), preferably between 1 and 6 and more preferably 1 or 2. A "linkage group" refers to a functional group which replaces a methylene in a straight chained hydrocarbyl. Examples of suitable linkage groups include a ketone ($-C(O)-$), alkene, alkyne, phenylene, ether ($-O-$), thioether ($-S-$), or amine ($-N(R^a)-$), wherein $R^a$ is defined below. A preferred linkage group is $-C(R_5R_6)-$, wherein $R_5$ and $R_6$ are defined above. Suitable substituents for an alkylene group and a hydrocarbyl group are those which do not substantially interfere with the anti-cancer activity of the bis(thiohydrazide) amides and taxanes. $R_5$ and $R_6$ are preferred substituents for an alkylene or hydrocarbyl group represented by Y.

An aliphatic group is a straight chained, branched or cyclic non-aromatic hydrocarbon which is completely saturated or which contains one or more units of unsaturation. Typically, a straight chained or branched aliphatic group has from 1 to about 20 carbon atoms, preferably from 1 to about 10, and a cyclic aliphatic group has from 3 to about 10 carbon atoms, preferably from 3 to about 8. An aliphatic group is preferably a straight chained or branched alkyl group, e.g., methyl, ethyl, n-propyl, iso-propyl, n-butyl, sec-butyl, tert-butyl, pentyl, hexyl, pentyl or octyl, or a cycloalkyl group with 3 to about 8 carbon atoms. A C1-C20 straight chained or branched alkyl group or a C3-C8 cyclic alkyl group is also referred to as a "lower alkyl" group.

The term "aromatic group" may be used interchangeably with "aryl," "aryl ring," "aromatic ring," "aryl group" and "aromatic group." Aromatic groups include carbocyclic aromatic groups such as phenyl, naphthyl, and anthracyl, and heteroaryl groups such as imidazolyl, thienyl, furanyl, pyridyl, pyrimidyl, pyranyl, pyrazolyl, pyrroyl, pyrazinyl, thiazole, oxazolyl, and tetrazole. The term "heteroaryl group" may be used interchangeably with "heteroaryl," "heteroaryl ring," "heteroaromatic ring" and "heteroaromatic group." The term "heteroaryl," as used herein, means a mono- or multi-cyclic aromatic heterocycle which comprise at least one heteroatom such as nitrogen, sulfur and oxygen, but may include 1, 2, 3 or 4 heteroatoms per ring. Aromatic groups also include fused polycyclic aromatic ring systems in which a carbocyclic aromatic ring or heteroaryl ring is fused to one or more other heteroaryl rings. Examples include benzothienyl, benzofuranyl, indolyl, quinolinyl, benzothiazole, benzooxazole, benzimidazole, quinolinyl, isoquinolinyl and isoindolyl.

The term "arylene" refers to an aryl group which is connected to the remainder of the molecule by two other bonds. By way of example, the structure of a 1,4-phenylene group is shown below:

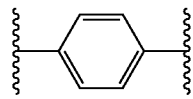

Substituents for an arylene group are as described below for an aryl group.

Non-aromatic heterocyclic rings are non-aromatic rings which include one or more heteroatoms such as nitrogen, oxygen or sulfur in the ring. The ring can be five, six, seven or eight-membered. Examples include tetrahydrofuranyl, tetrahydrothiophenyl, morpholino, thiomorpholino, pyrrolidinyl, piperazinyl, piperidinyl, and thiazolidinyl.

Suitable substituents on an aliphatic group (including an alkylene group), non-aromatic heterocyclic group, benzylic or aryl group (carbocyclic and heteroaryl) are those which do not substantially interfere with the anti-cancer activity of the bis(thiohydrazide) amides and taxanes. A substituent substantially interferes with anti-cancer activity when the anti-cancer activity is reduced by more than about 50% in a compound with the substituent compared with a compound without the substituent. Examples of suitable substituents include —$R^a$, —OH, —Br, —Cl, —I, —F, —O$R^a$, —O—CO$R^a$, —CO$R^a$, —CN, —NO$_2$, —COOH, —SO$_3$H, —NH$_2$, —NH$R^a$, —N($R^a R^b$), —COO$R^a$, —CHO, —CONH$_2$, —CON$R^a$, —CON($R^a R^b$), —NHCO$R^a$, —N$R^c$CO$R^a$, —NHCONH$_2$, —NHCON$R^a$H, —NHCON($R^a R^b$), —N$R^c$CONH$_2$, —N$R^c$CON$R^a$H, —N$R^c$CON($R^a R^b$), —C(=NH)—NH$_2$, C(=NH)—NH$R^a$, —C(=NH)—N($R^a R^b$), —C(=N$R^c$)—NH$_2$, —C(=N$R^c$)—NH$R^a$, —C(=N$R^c$)—N($R^a R^b$), —NH—C(=NH)—NH$_2$, —NH—C(=NH)NH$R^a$, —NH—C(=NH)—N($R^a R^b$), —NH—C(=N$R^c$)—NH$_2$, —NH—C(=N$R^c$)—NH$R^a$, —NH—C(=N$R^c$)—N($R^a R^b$), —N$R^d$H—C(=NH)—NH$_2$, —N$R^d$—C(=NH)—NH$R^a$, N$R^d$—C(=NH)—N($R^a R^b$), N$R^d$—C(=N$R^c$)—NH$_2$, —N$R^d$—C(=N$R^c$)—NH$R^a$, —N$R^d$—C(=N$R^c$)—N($R^a R^b$), —NHNH$_2$, NHNH$R^a$, —NH$R^a R^b$, —SO$_2$NH$_2$, —SO$_2$NH$R^a$, —SO$_2$N$R^a R^b$, —CH=CH$R^a$, —CH=C$R^a R^b$, —C$R^c$=C$R^a R^b$, —C$R^c$=CH$R^a$, —C$R^c$=C$R^a R^b$, —CC$R^a$, —SH, —S$R^a$, —S(O)$R^a$, and —S(O)$_2 R^a$. $R^a$-$R^d$ are each independently an alkyl group, aromatic group, non-aromatic heterocyclic group or —N($R^a R^b$), taken together, form an optionally substituted non-aromatic heterocyclic group. The alkyl, aromatic and non-aromatic heterocyclic group represented by $R^a$-$R^d$ and the non-aromatic heterocyclic group represented by —N($R^a R^b$) are each optionally and independently substituted with one or more groups represented by $R^\#$.

$R^\#$ is $R^+$, —O$R^+$, —O(haloalkyl), —S$R^+$, —NO$_2$, —CN, —NCS, —N($R^+$)$_2$, —NHCO$_2 R^+$, —NHC(O)$R^+$, —NHNHC(O)$R^+$, —NHC(O)N($R^+$)$_2$, —NHNHC(O)N($R^+$)$_2$, —NHNHCO$_2 R^+$, —C(O)C(O)$R^+$, —C(O)CH$_2$C(O)$R^+$, —CO$_2 R^+$, —C(O)$R^+$, —C(O)N($R^+$)$_2$, —OC(O)$R^+$, —OC(O)N($R^+$)$_2$, —S(O)$_2 R^+$, —SO$_2$N($R^+$)$_2$, —S(O)$R^+$, —NHSO$_2$N($R^+$)$_2$, —NHSO$_2 R^+$, —C(=S)N($R^+$)$_2$, or —C(=NH)—N(R)$_2$.

$R^+$ is —H, a C1-C4 alkyl group, a monocyclic heteroaryl group, a non-aromatic heterocyclic group or a phenyl group optionally substituted with alkyl, haloalkyl, alkoxy, haloalkoxy, halo, —CN, —NO$_2$, amine, alkylamine or dialkylamine. Optionally, the group —N($R^+$)$_2$ is a non-aromatic heterocyclic group, provided that non-aromatic heterocyclic groups represented by $R^+$ and —N($R^+$)$_2$ that comprise a secondary ring amine are optionally acylated or alkylated.

Preferred substituents for a phenyl group, including phenyl groups represented by $R_1$-$R_4$, include C1-C4 alkyl, C1-C4 alkoxy, C1-C4 haloalkyl, C1-C4 haloalkoxy, phenyl, benzyl, pyridyl, —OH, —NH$_2$, —F, —Cl, —Br, —I, —NO$_2$ or —CN.

Preferred substituents for an aliphatic group, including aliphatic groups represented by $R_1$-$R_4$, include C1-C4 alkyl, C1-C4 alkoxy, C1-C4 haloalkyl, C1-C4 haloalkoxy, phenyl, benzyl, pyridyl, —OH, —NH$_2$, —F, —Cl, —Br, —I, —NO$_2$ or —CN.

Preferred substituents for a cycloalkyl group, including cycloalkyl groups represented by $R_1$ and $R_2$, are alkyl groups, such as a methyl or ethyl groups.

It will also be understood that certain compounds employed in the invention may be obtained as different stereoisomers (e.g., diastereomers and enantiomers) and that the invention includes all isomeric forms and racemic mixtures of the disclosed compounds and methods of treating a subject with both pure isomers and mixtures thereof, including racemic mixtures. Stereoisomers can be separated and isolated using any suitable method, such as chromatography.

EXEMPLIFICATION

Examples 1-3

Preparation of Disodium Bis(Thio-Hydrazide Amide) Solution

A sample of a bis(thio-hydrazide amide) (Compound 1, 15 grams) was combined with 40 mL of absolute ethanol to form a mixture as a slurry. Aqueous sodium hydroxide (3.0 grams NaOH in 3.0 mL H$_2$O) was added to the mixture with stirring at room temperature, and the mixture was cooled to not exceed 35 degrees C. The aqueous sodium hydroxide addition vessel was rinsed with 1 mL of water and 5 mL of ethanol, and the rinses were added to the mixture. After addition, the mixture was stirred for 110 minutes. The resulting yellow disodium bis(thio-hydrazide amide) solution was separated into three equal portions for the following examples.

Example 1

63% Yield of Bis(Thio-Hydrazide Amide) Disodium Salt

A one-third portion of the above yellow disodium bis(thio-hydrazide amide) solution was combined with 17 mL of methyl tert-butyl ether and stirred for 60 minutes (precipitation occurred in less than 30 minutes). The resulting slurry was filtered, washed with 10 mL of a 1:1 mixture of ethyl acetate:methyl tert-butyl ether, followed by 5 mL of ethyl acetate. Residual solvent was removed by vacuum to give 3.51 grams (63%) of the disodium salt of Compound (1) as a pale yellow solid. A yellow contaminant was visible.

Example 2

87% Yield of Pure Bis(Thio-Hydrazide Amide) Disodium Salt

A one-third portion of the above yellow disodium bis(thio-hydrazide amide) solution was combined with 17 mL of methyl tert-butyl ether and stirred for 60 minutes (precipitation occurred in less than 30 minutes). An additional 17 mL of methyl tert-butyl ether was added to the resulting thick slurry, and was stirred for an additional 14 hours. The resulting slurry was filtered, washed with 10 mL of a 1:1 mixture of ethyl acetate:methyl tert-butyl ether, followed by 10 mL of ethyl acetate. Residual solvent was removed by vacuum to give 4.84 grams (87%) of the disodium salt of Compound (1) as a pale yellow solid. No yellow contaminant was visible.

Example 3

96% Yield of Pure Bis(Thio-Hydrazide Amide) Disodium Salt

A one-third portion of the above yellow disodium bis(thio-hydrazide amide) solution was combined with 17 mL of methyl tert-butyl ether and stirred for 60 minutes (precipitation occurred in less than 30 minutes). An additional 34 mL of methyl tert-butyl ether was added to the resulting thick slurry, and was stirred for an additional 14 hours. The resulting slurry was filtered, washed with 10 mL of a 1:1 mixture of ethyl acetate:methyl tert-butyl ether, followed by 10 mL of ethyl acetate. Residual solvent was removed by vacuum to give 5.35 grams (96%) of the disodium salt of Compound (1) as a pale yellow solid. No yellow contaminant was visible.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of preparing a pharmaceutically acceptable bis(thio-hydrazide amide) disalt, comprising the steps of:
    combining a neutral bis(thio-hydrazide amide) represented by the following structural formula:

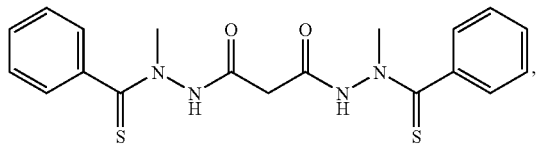

an organic solvent selected from a C1-C4 aliphatic alcohol, a C1-C4 aliphatic ketone, a C2-C4 aliphatic ether, a glycol and an alkyl glycol ether, and a base to form a bis(thio-hydrazide amide) disalt solution; and
    combining the solution and methyl tert-butyl ether, thereby precipitating the bis(thio-hydrazide amide) disalt.

2. The method of claim 1, wherein at least about two molar equivalents of the base are employed for each molar equivalent of neutral bis(thio-hydrazide amide).

3. The method of claim 2, wherein the organic solvent is water-miscible.

4. The method of claim 1, wherein the organic solvent is selected from methanol, ethanol, 1-propanol, 2-propanol, 1-butanol, tert-butyl alcohol, acetone, and methyl ethyl ketone.

5. The method of claim 4, wherein the organic solvent is selected from methanol, ethanol, acetone, and methyl ethyl ketone.

6. The method of claim 2, wherein the base is an amine; an ammonium hydroxide; an alkali metal hydroxide, an alkali metal C1-C6 alkoxide, or an alkali metal amide.

7. The method of claim 6, wherein the base is sodium hydroxide, potassium hydroxide, sodium C1-C6 alkoxide, potassium C1-C6 alkoxide, sodium amide, or potassium amide.

8. The method of claim 6, wherein the base is selected from sodium hydroxide, sodium methoxide, or sodium ethoxide.

9. The method of claim 2, wherein the base is an alkali metal hydride, an alkyl alkali metal, or an aryl alkali metal.

10. The method of claim 9, wherein the base is lithium hydride, sodium hydride, potassium hydride, butyllithium, butylsodium, butylpotassium, phenyllithium, phenylsodium, or phenylpotassium.

11. The method of claim 1, wherein the neutral bis(thio-hydrazide amide) is first combined with the organic solvent to forming a mixture, and the base is added to the mixture to form the bis(thio-hydrazide amide) disalt solution.

12. The method of claim 1, wherein between about 0.25 and about 2.5 moles of the neutral bis(thio-hydrazide amide) are combined per each liter of organic solvent.

13. The method of claim 12, wherein between about 0.75 and about 1.5 moles of the neutral bis(thio-hydrazide amide) are combined per each liter of organic solvent.

14. The method of claim 12, wherein between about 2 and about 5 molar equivalents of the base are employed.

15. The method of claim 14, wherein between about 2.0 and about 2.5 molar equivalents of the base are employed.

16. The method of claim 14, wherein about 1 mole of the neutral bis(thio-hydrazide amide) is combined per each liter of the organic solvent.

17. The method of claim 16, wherein the organic solvent is ethanol.

18. The method of claim 17, wherein the base is about 2 molar to about 5 molar aqueous sodium hydroxide.

19. The method of claim 16, wherein the organic solvent is acetone.

20. The method of claim 19, wherein the base is about 2 molar to about 5 molar ethanolic sodium ethoxide.

21. A method of preparing a bis(thio-hydrazide amide) disalt, comprising the steps of:
    combining a neutral bis(thio-hydrazide amide) represented by the following structural formula:

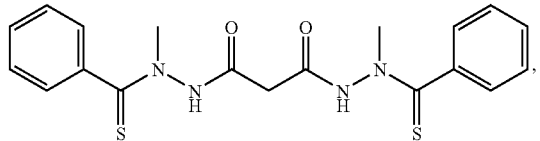

and an organic solvent selected from methanol, ethanol, acetone, and methyl ethyl ketone to make a mixture;
    adding at least two equivalents of a base selected from sodium hydroxide, potassium hydroxide, sodium methoxide, potassium methoxide, sodium ethoxide and potassium ethoxide to the mixture, thereby forming a bis(thio-hydrazide amide) disalt solution; and
    combining the solution and methyl tert-butyl ether to precipitate the disalt of the bis(thio-hydrazide amide) from the bis(thio-hydrazide amide) solution.

22. The method of claim 21, wherein the organic solvent is acetone.

23. The method of claim 21, wherein the base is ethanolic sodium ethoxide.

24. The method of claim 21, wherein the organic solvent is ethanol.

25. The method of claim 21, wherein the base is aqueous sodium hydroxide.

* * * * *